(12) United States Patent
Hughes (10) Patent No.: US 8,906,654 B2
(45) Date of Patent: Dec. 9, 2014

(54) KLUYVEROMYCES MARXIANUS STRAINS AND METHOD OF USING STRAINS

(71) Applicant: The United States of America, as represented by the Secretary of Agriculture, Washington, DC (US)

(72) Inventor: Stephen R. Hughes, Peoria, IL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 50 days.

(21) Appl. No.: 13/747,691

(22) Filed: Jan. 23, 2013

(65) Prior Publication Data

US 2014/0206053 A1     Jul. 24, 2014

(51) Int. Cl.
*C12N 1/16* (2006.01)

(52) U.S. Cl.
CPC .......................................... *C12N 1/16* (2013.01)
USPC ...................................... 435/161; 435/255.1

(58) Field of Classification Search
CPC ........ C12N 15/815; C12N 15/81; C12N 1/16; C12P 7/06; C12P 7/18; Y02E 50/17
USPC ............................................... 435/161, 255.1
See application file for complete search history.

(56) References Cited

PUBLICATIONS

Pang et al., Biotechnol. Lett. 32, 1847-1852 (2010).*

* cited by examiner

*Primary Examiner* — Chih-Min Kam
(74) *Attorney, Agent, or Firm* — John Fado; Albert Y. Tsui; Lesley Shaw (57) ABSTRACT

Described are novel *Kluyveromyces marxianus* strains NRRL Y-50798 and Y-50799, that were obtained by UV-C irradiation of wild-type *K. marxianus* NRRL Y-1109 cultures. The UV-C-mutagenized strains were incubated under anaerobic conditions on xylose or glucose medium for a period of 5 months at 46° C. before being selected. These mutagenized strains have potential application in large-scale industrial conversion of lignocellulosic sugars to fuel ethanol given their ability to ferment at temperatures at 46° C. and above.

9 Claims, 7 Drawing Sheets

SEQUENCE LISTING

<160> NUMBER OF SEQ ID NOS: 1

<210> SEQ ID NO 1
<211> LENGTH: 15
<212> TYPE: DNA
<213> ORGANISM: Artificial Sequence
<220> FEATURE:
<223> OTHER INFORMATION: PCR Primer

<400> SEQUENCE: 1
cagcagcagc agcag                                            15

KLUYVEROMYCES MARXIANUS STRAINS AND METHOD OF USING STRAINS

FIELD OF INVENTION

The present invention is for novel *Kluyveromyces marxianus* yeast strains that produce ethanol. More specifically, the mutagenized yeast strains are able to grow aerobically on glucose at 47° C., and anaerobically at 46° C. on glucose, galactose, galacturonic acid, and pectin. Of particular interest, yeast strain NRRL Y-50798 was able to grow anaerobically on xylose at 46° C.

BACKGROUND OF INVENTION

The United States Environmental Protection Agency has issued a rule to increases the volume requirements for total renewable fuel to 20.5 billion gallons and for cellulosic biofuel to 3.0 billion gallons by 2015. To meet these mandates, it will be necessary to use cellulosic biomass, an abundant and renewable carbon source, as a feedstock.

Currently, *S. cerevisiae* is frequently used to ferment biomass sources to produce fuel ethanol. One of the drawbacks in using conventional *S. cerevisiae* strains is that *S. cerevisiae* strains typically optimally operate between 25° C. and 30° C. to produce ethanol in industrial fermentation systems. The produced heat from the fermentation system generally requires some means of cooling the system to the optimal temperature range. In the absence of cooling, heat stress on the yeast strain reduces the production yield. Additionally, a yeast strain that optimally ferments at higher temperatures would improve the efficiency of simultaneous saccharification and fermentation, and allow for the continuous ethanol removal by evaporation under reduced pressure. As such, there is a need to develop a heat tolerant yeast strain to take advantage of producing fuel ethanol at higher temperatures.

The yeast strain, *Kluyveromyces marxianus*, has an advantage over typical *Saccharomyces cerevisiae* with respect to higher operating temperature ranges in that *Kluyveromyces marxianus* has been reported to grow at 47° C. and above (Nonklang, S. et al., *Appl. Environ. Microbiol.* 2008, 74(24), 7514-7521) and produce ethanol at temperatures above 40° C. (Fonseca, G. G., et al., *Appl. Microbiol. Biotechnol.* 2008, 79, 339-354).

Additionally, *K. marxianus* offers other benefits compared to typical *S. cerevisiae* strains. Other benefits include the ability to grow on a wide variety of substrates not utilized by *S. cerevisiae* such as xylose, xylitol, cellobiose, lactose, arabinose, and glycerol (Nonklang, S.; Abdel-Banat, B. M. A.; Cha-aim, K.; Moonjai, N.; Hoshida, H.; Limtong, S.; Yamada, M.; Akada, R. High-temperature ethanol fermentation and transformation with linear DNA in the thermotolerant yeast *Kluyveromyces marxianus* DMKU3-1042 *Appl. Environ. Microbiol.* 2008, 74(24), 7514-7521 and Rodrussamee, N.; Lertwattanasakul, N.; Hirata, K.; Suprayogi; Limtong, S.; Kosaka, T.; Yamada, M. Growth and ethanol fermentation ability on hexose and pentose sugars and glucose effect under various conditions in thermotolerant yeast *Kluyveromyces marxianus*. *Appl. Microbiol. Biotechnol.* 2011, 90, 1573-1586). *K. marxianus* also grows on sucrose, raffinose, and inulin at 45° C. under a static condition even when glucose is present unlike *S. cerevisiae*. Given the benefits offered by *K. marxianus*, further evaluation of various strains is warranted.

BRIEF DESCRIPTION OF THE DRAWINGS

The present invention together with the above and other objects and advantages may best be understood from the following detailed description of the embodiment of the invention illustrated in the drawings, wherein.

DEPOSIT OF BIOLOGICAL MATERIAL

Strains Y-50798 and Y-50799 are identified as variants of *Kluyveromyces marxianus* based on variable nucleotide tandem repeat (VNTR) analysis. Both NRRL Y-50798 and NRRL Y-50799 were deposited on Jan. 15, 2013, under the provisions of the Budapest Treaty in the Agricultural Research Culture Collection (NRRL) in Peoria, Ill., and have been assigned Accession Nos. NRRL Y-50798 and NRRL Y-50799.

The subject cultures have been deposited under conditions that assure that access to the cultures will be available during the pendency of this patent application to one determined by the Commissioner of Patents and Trademarks to be entitled thereto under 37 CFR §1.14 and 35 USC §122. The deposits are available as required by foreign patent laws in countries wherein counterparts of the subject application, or its progeny, are filed. However, it should be understood that the availability of the deposits does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposits, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

As described herein, *Kluyveromyces marxianus* strain NRRL Y-50798 is also referred to as strain 7-1. *Kluyveromyces marxianus* strain NRRL Y-50799 is also referred to as strain 8-1.

BRIEF DESCRIPTION OF THE SEQUENCES

The invention can be more fully understood from the following detailed description and the accompanying sequence descriptions, which form a part of this application.

SEQ. ID. NO. 1: CAGCAGCAGCAGCAG is a PCR primer.

DETAILED DESCRIPTION OF THE INVENTION

Disclosed herein is an isolated *Kluyveromyces marxianus* having been deposited with the United States Department of Agriculture, Agricultural Research Patent Culture Collection as Accession Deposit Number NRRL Y-50798. Also disclosed is an isolated *Kluyveromyces marxianus* having been deposited with the United States Department of Agriculture, Agricultural Research Patent Culture Collection as Accession Deposit Number NRRL Y-50799.

Disclosed is an isolated *Kluyveromyces marxianus* having been deposited with the United States Department of Agriculture, Agricultural Research Patent Culture Collection as Accession Deposit Number NRRL Y-50798.

Also disclosed is an isolated *Kluyveromyces marxianus* having been deposited with the United States Department of Agriculture, Agricultural Research Patent Culture Collection as Accession Deposit Number NRRL Y-50799.

Also disclosed is a method of producing ethanol comprising culturing yeast strain NRRL Y-50798 or NRRL Y-50799 under suitable conditions for a period of time sufficient to allow fermentation of at least a portion of feedstock to ethanol. In one embodiment of the method, the conditions include hexose sugars. In another embodiment of the method, the conditions include pentose sugars. In yet another embodiment of the method, the yeast strains ferment glucose and xylose at aerobic conditions. In yet another embodiment of the method, the feedstock contains galacturonic acid. In another embodiment of the method, the strain NRRL Y-50798 or Y-50799 grow on a substrate consisting essentially of galacturonic acid, pectin, glucose, arabinose, xylose, and galactose under aerobic conditions. In another embodiment of the method, the strain NRRL Y-50798 or Y-50799 grow on a substrate comprising of guar.

Generation of Isolates 7-1 and 8-1 (NRRL Y-50798 and Y-50799)

Figure 1:
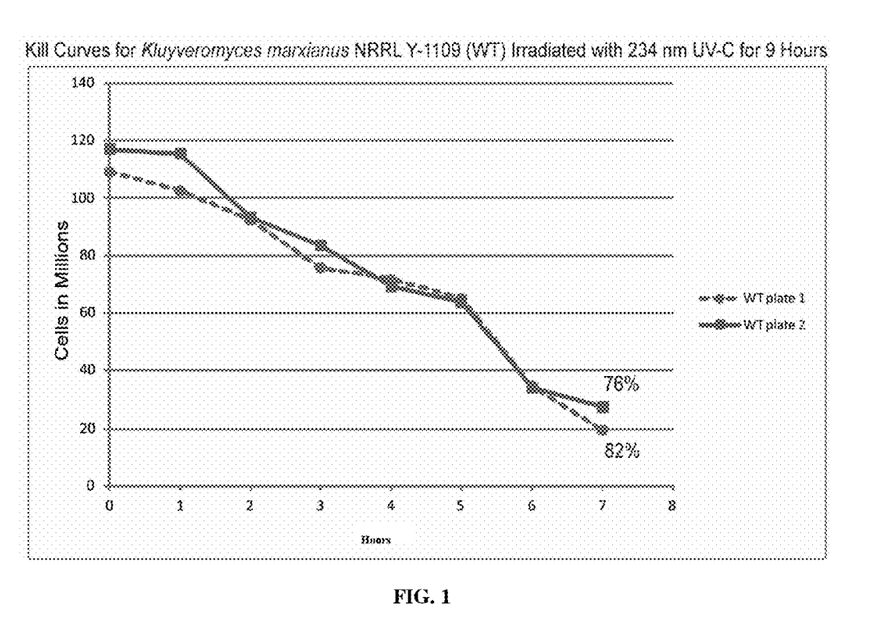
FIG. 1 is a graph depicting cell kill curves for *Kluyveromyces marxianus* NRRL Y-1109 wild-type (WT) strain irradiated at 14 cm for 9 h with UV-C 234 nm.

Duplicate 2-L Fernbach flasks were prepared by adding 1 L of YM medium [0.3% yeast extract, 0.3% malt extract, 0.5% peptone (Becton, Dickinson and Company, Franklin Lakes, N.J., USA), and 1.0% dextrose (Sigma Aldrich, St. Louis, Mo., USA)] to each flask and inoculating with 20 mL of a culture of wild-type *K. marxianus* NRRL Y-1109 (USDA, ARS Culture Collection) grown on YM medium in a 100-mL flask at 28° C. for 2 days. The Fernbach flasks were incubated at 28° C. for 2 days at 100 rpm. The culture from each flask was divided into two Beckman 500-mL spin bottles and pelleted in a Beckman Avanti J20 centrifuge (Beckman Coulter, Inc., Indianapolis, Ind., USA) at 20° C. for 20 minutes at 2056×g. Cell pellets were washed and resuspended in 50 mL of sterile water. A 25-mL aliquot was taken from each resuspension and placed into a Marsh RR-0014 deep trough plate with baffled bottom (Marsh Biomedical Products, Inc., Rochester, N.Y., USA). Before irradiation, a 10-µL sample was taken from the resuspension in the trough plates, diluted to $10^{-5}$, and evaluated using a Reichert Neubauer/Bright-Line® Hemacytometer (American Optical Corp., Buffalo, N.Y., USA) to obtain an estimate of cell density. The cells were irradiated for 9 hours with 234 nm UV-C radiation [UVP, LLC Light Table (inverted); Upland, Calif., USA] at a distance of 14 cm above the plates. Samples (100 µL) were taken every hour during irradiation, diluted to $10^{-4}$, plated, and the surviving colonies counted to determine the kill curve. The progress of the irradiation was monitored by taking samples every hour during irradiation, diluting and plating them, and counting the surviving colonies to determine the kill curve. The results show that 80% mortality is obtained after 9 hours of irradiation (FIG. 1). Strains Y-50798 and Y-50799 were derived from the 82% kill plate, WT plate 1 of FIG. 1.

An automated protocol on a robotic workcell (as described in Hughes, S. R., et al., *J. Assoc. Lab. Autom.* 2011, 16, 292-307 and incorporated herein by reference) was used after irradiation to spread 600-µL aliquots from each trough plate onto 128×96 mm Omni Tray plates (Thermo Fisher Scientific, Waltham, Mass., USA) containing YM medium [0.3% yeast extract, 0.3% malt extract, 0.5% peptone, 2% Bacto™ Agar (Becton, Dickinson and Company, Franklin Lakes, N.J., USA), and 1.0% dextrose] or 2% xylose complete minimal medium plus all amino acids [1.4 g yeast synthetic drop-out medium supplement, 0.06 g L-leucine, 0.04 g L-tryptophan, 0.02 g L-histidine, 0.02 g L-uracil; 20 g D-xylose (Sigma Aldrich, St. Louis, Mo., USA), 20 g Bacto Agar; and 6.7 g yeast nitrogen base without amino acids (Sigma Aldrich, St. Louis, Mo., USA) per liter]. The plates from several passive and active stackers were moved to the liquid handler in a scheduled fashion where they were spotted with medium and then with irradiated culture from the Marsh deep trough plates on the deck. The spread plates (a total of 192 plates, 96 from each trough plate) were wrapped and placed into Mitsubishi anaerobic chambers (Mitsubishi Gas Chemical America, Inc., New York, N.Y., USA) containing an Anaero-Pack dry chemical system (Sigma Fluka, Buchs, Switzerland) at 46° C. for 5 months.

Two YM plates each contained one growing colony when the spread plates were unwrapped. Duplicate samples were picked manually from these colonies, designated strains Y-50798 and Y-50799, respectively, and spread onto plates containing YM or YPD [1.0% yeast extract, 2.0% Bacto Peptone, 2.0% Bacto Agar, and 2.0% D-glucose (Sigma Aldrich, St. Louis, Mo., USA)] medium or 2% xylose complete minimal medium plus all amino acids, and the plates were incubated at 46° C. for 2 weeks anaerobically to isolate individual colonies. Four colonies were picked manually from each of the re-spread anaerobic plates onto plates containing YM, YPD, or xylose complete minimal medium plus all amino acids (one sample per plate, 4 samples per medium) and incubated aerobically at 28° C. for 3 days to confirm that strains Y-50798 and Y-50799 were still capable of aerobic growth.

Samples were also taken and plated on YPD medium for evaluation of growth at 30° C. and 47° C. to compare thermotolerance of mutant strains to that of wild-type *K. marxianus* NRRL Y-1109. The mutant strains were further evaluated for growth on various substrates aerobically and anaerobically at 46° C. in comparison to wild-type *K. marxianus* NRRL Y-1109 and to *S. cerevisiae* NRRL Y-2043 in the following examples.

Example 1

Fermentation in 2-L Fernbach Flask

Fermentation experiments using wild-type *K. marxianus* NRRL Y-1109, mutant strains Y-50798 and Y-50799, and *S. cerevisiae* NRRL Y-2043 were performed in 2-L Fernbach flasks containing YM liquid medium maintained at 46° C. A liquid preculture was grown in a 100-mL flask on YM medium for 2 days at 28° C. The density of the preculture was adjusted to an absorbance equivalent to 1.0 at 660 nm (Beckman DU 800; Beckman Coulter, Inc., Indianapolis, Ind., USA) and 20 mL were added to 1 liter of YM medium in the Fernbach flask. The fermentation was carried out at 46° C. at 100 rpm for 30 hours. The absorbance at 660 nm and ethanol production were measured at approximately 10-hour intervals.

Figure 3:
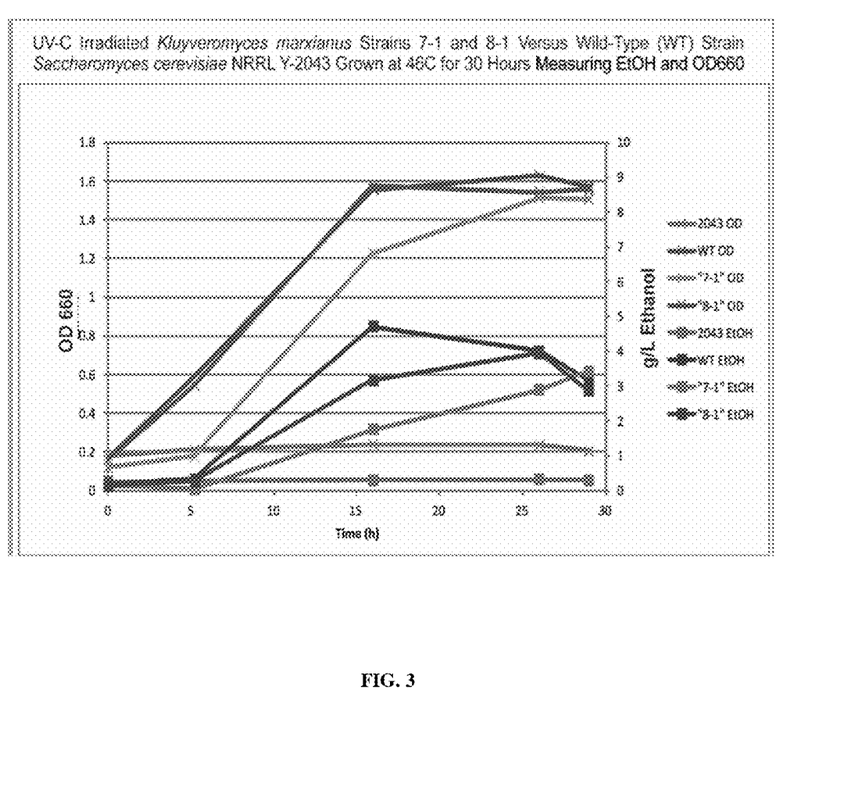
FIG. 3 is a graph depicting ethanol production (g/L) and cell growth (absorbance at 660 nm) for wild-type (WT) *Kluyveromyces marxianus* NRRL Y-1109, *K. marxianus* mutant strains NRRL Y-50798 and Y-50799, and *Saccharomyces cerevisiae* NRRL Y-2043 for 30 hours at 46° C. in 1 liter YM medium (10 g/L glucose) under microaerophilic conditions in a 2-L Fernbach flask.

Ethanol production (g/L) and cell growth (absorbance at 660 nm) were monitored during a 30-hour fermentation experiment in a 2-L Fernbach flask in YM medium (10 g/L glucose) at 46° C. for wild-type *K. marxianus* NRRL Y-1109, mutant strains Y-50798 and Y-50799, and *S. cerevisiae* NRRL Y-2043 (FIG. 3). *S. cerevisiae* NRRL Y-2043 did not grow at 46° C. and therefore no ethanol was produced. Cell growth for wild-type *K. marxianus* NRRL Y-1109 and mutant strain Y-50799 rose from initial OD660 values of about 0.16 up to 0.55 at 5 hours then to 1.57 at 15 hours and remained essentially at that level for the remainder of the 30-hour experiment. Cell growth for mutant strain Y-50798 showed a delayed entry into log phase with the OD 660 value remaining at 0.18 until 5 hours, then rising to 1.22 at 15 hours showing a growth rate (based on slope) similar to that of wild-type Y-1109 and Y-50799. Growth was still increasing at 15 hours and the OD660 value reached 1.51 at 26 hours, similar to wild-type Y-1109 and Y-50799. For all three strains, ethanol production started at 5 hours. The ethanol level for wild-type *K. marxianus* NRRL Y-1109 reached a maximum of 4.7 g/L at 15 hours, after which it decreased steadily to 3.1 g/L at 30 hours. The ethanol level for mutant strain Y-50799 rose more slowly than for the wild-type strain, reaching a maximum of 3.9 g/L at 25 hours, after which it decreased steadily to 2.9 g/L at 30 hours. Ethanol production for mutant strain Y-50798 increased more slowly than mutant strain Y-50799 but was still rising at the end of the experiment (30 hours) where it was 3.4 g/L.

Example 2

Scanning Electron Images of NRRL Y-1109 and Mutant Strains Y-50798 and Y-50799

NRRL Y-1109, Mutant Strains Y-50798 and Y-50799 cells from YPD [1.0% yeast extract, 2.0% Bacto Peptone, and 2.0% D-glucose (Sigma Aldrich, St. Louis, Mo., USA)], 2% xylose [1.4 g yeast synthetic drop-out medium supplement, 0.06 g L-leucine, 0.04 g L-tryptophan, 0.02 g L-histidine, 0.02 g uracil, 20 g D-xylose, and 6.7 g yeast nitrogen base without amino acids (Sigma Aldrich, St. Louis, Mo., USA) per liter] or YPGA [1.0% yeast extract, 2.0% Bacto Peptone, and 2.0% galacturonic acid (Sigma Aldrich, St. Louis, Mo., USA)] liquid medium incubated aerobically at 46° C. for 12 hours were suspended in saline (0.85% NaCl) and centrifuged to remove residual medium. Following a modified procedure of Bang and Pazirandeh (Bang, S. S., et al., *J. Microencapsul.* 1999, 16(4), 489-499 and incorporated herein by reference), the cell pellet was suspended and fixed in 2.5% glutaraldehyde prepared in 100 mM cacodylate buffer, pH 7.2, for one hour on ice. To remove remaining glutaraldehyde, the cells were rinsed with the buffer twice and then with distilled water once, allowing several minutes for each step. The cells were dehydrated, respectively, in solutions containing 50%, 70%, 80%, and 100% ethanol successively for 15 minutes for each treatment. Cells were mounted on an aluminum stub and placed in a desiccator to dry overnight or until needed. The samples were subjected to scanning electron microscopy and analysis (Zeiss Supra 40 VP).

Figure 4:
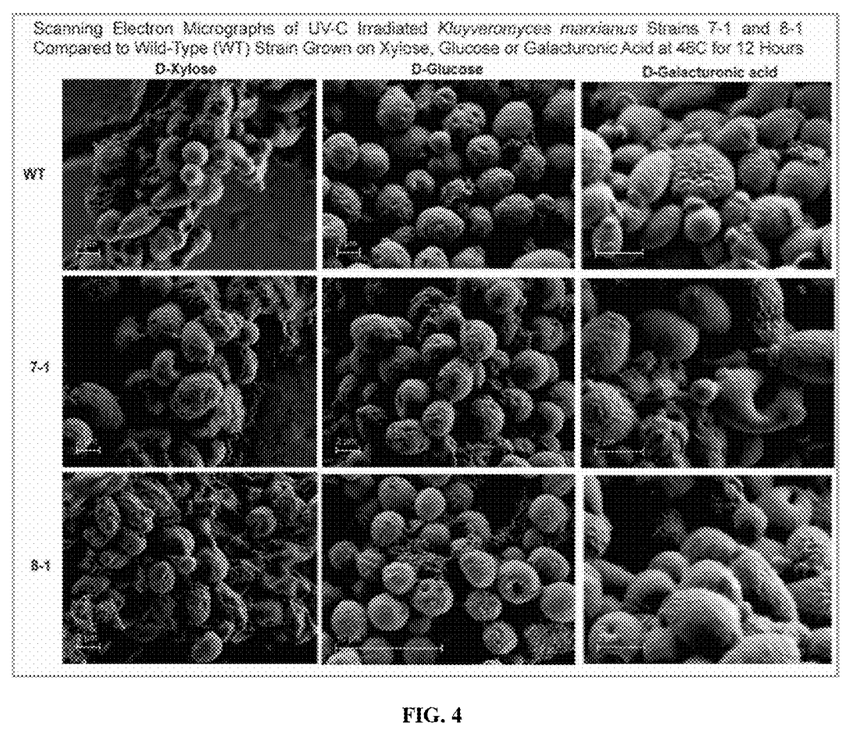
FIG. 4 depicts scanning electron micrographs of *Kluyveromyces marxianus* mutant strains Y-50798 and Y-50799 compared to *K. marxianus* NRRL Y-1109 wild-type (WT).

Cells from cultures of *K. marxianus* wild-type and mutant strains grown using glucose, xylose, or galacturonic acid as substrates were examined using scanning electron microscopy (FIG. 4). The scanning electron micrographs of the wild-type *K. marxianus* NRRL Y-1109 and mutant strains grown on glucose show that the cells were generally similar in size, shape, and surface features. On the other hand, the micrographs of cells from these strains grown on xylose show that the cells of mutant strain Y-50798 are larger than those of the wild-type strain and that more of the Y-50798 cells have cratered surfaces compared to the wild-type cells. The cells of mutant strain Y-50799 grown on xylose are smaller than those of mutant strain Y-50798, however the surfaces are not only cratered but also wrinkled, and the shapes of the cells are flattened and distorted compared to the shapes of wild-type and Y-50798 cells. The micrographs of cells from strains grown on galacturonic acid, show that most of the cells of the wild-type strain have a relatively smooth, non-cratered surface and are urn-shaped with bud-like projections at the tops. In contrast, the cells of mutant strains Y-50798 and Y-50799 are larger and their surfaces are more cratered than those of the wild-type strain. The shapes of most of the cells of strain Y-50799 grown on galacturonic acid are round with dimples, which are notably different from the urn-shaped cells with bud-like projections observed in the micrograph for the wild-type strain.

Example 3

DNA Fingerprinting

Variable nucleotide tandem repeat (VNTR) PCR analysis was performed to detect differences in genomic DNA sequences using as PCR primer the 15-base pair (bp) 5×CAG repeat sequence. Genomic DNA from wild-type *K. marxianus* NRRL Y-1109 and mutant strains Y-50798 or Y-50799 was isolated from a 1-mL sample of a 2-day 37° C. culture in YPD liquid medium in a 1.5-mL polypropylene tube. The samples were vortexed for 30 seconds and then centrifuged at 15,800×g for 2 minutes (Thermo Micromax Microcentrifuge; Thermo Fisher Scientific, Waltham, Mass., USA). The supernatant was decanted and an additional 1 mL of the culture was added to the tubes. The tubes were vortexed for 30 seconds and then centrifuged at 15,800×g for 2 minutes. The supernatant was decanted and 400 µL of water were added. The mixture was boiled for 10 minutes followed by addition of 400 µL of phenol solution (saturated, pH 6.6; AMRESCO LLC, Solon, Ohio, USA). The tubes were vortexed for 30 seconds and then centrifuged at 15,800×g for 2 minutes. The aqueous phase was transferred by pipet to new 1.5-mL tubes and 400 µL of phenol:chloroform:isoamyl alcohol (25:24:1; tris buffer to pH 8.05; AMRESCO, LLC; Solon, Ohio, USA) were added. The tubes were vortexed for 30 seconds and then centrifuged at 15,800×g for 2 minutes. The aqueous phase was transferred by pipet to new 1.5-mL tubes and 400 µL of ethyl ether (water-saturated; Avantor Performance Materials, formerly J.T. Baker, Phillipsburg, N.J., USA) were added. The tubes were vortexed for 30 seconds and then centrifuged at 15,800×g for 2 minutes. The organic phase was removed by pipet and discarded, and 40 µL of 3 M sodium acetate, pH 5.2 (Sigma Aldrich, St. Louis, Mo., USA) were added to the remaining solution. The tubes were vortexed for 90 seconds and 1.5 mL of cold 100% ethanol was added. The tubes were placed into a −80° C. freezer overnight. After removal from the freezer, the tubes were centrifuged for 10 minutes at 15,800×g, and the liquid decanted. One mL of cold 70% aqueous ethanol solution was added and the tubes centrifuged for 10 minutes at 15,800×g. The liquid was removed with a pipet leaving the clear pellet on the bottom. The material was dried in a Savant SPD 2010 SpeedVac System (Thermo Fisher Scientific, Waltham, Mass., USA) for 5 minutes at 45° C. and 8 psi. The tubes were removed from the dryer, 70 µL of water were added, and the tubes were allowed to stand for 10 minutes. The concentration of genomic DNA obtained was determined by densitometry using an AlphaImager™ 3400 (Alpha Innotech Corporation, San Diego, Calif., USA).

The PCR mixture contained 2 µL genomic DNA (0.5 mg/mL), 32.5 µL water, 10 µL 5× Phusion HF Buffer with $MgCl_2$, 1 µL 10 mM dNTPs, 4 µL (0.1 mg/mL) VNTR oligonucleotide primer (5'CAGCAGCAGCAGCAG3') (SEQ. ID. NO. 1) and 0.5 µL Phusion Enzyme (Finnzymes Phusion High-Fidelity PCR kit; New England Biolabs, Ipswich, Mass., USA). The PCR reaction was prepared in a Phenix MPC-3420 96-well PCR plate (Phenix Research Products, Candler, N.C., USA) on ice and was carried out in a PTC-225 Tetrad Thermal Cycler (Bio-Rad Laboratories, Hercules, Calif., USA) using the following conditions: hold at 95° C. for 5 minutes, cycle at 95° C. for 1 minute, 42° C. for 1 minute, 72° C. for 1 minute, repeated for 30 times, followed by 72° C. for 5 minutes and a 4° C. hold. The procedure amplified the genomic sequence between two VNTR sequences to determine alterations in the microsatellite or minisatellite regions in the genome. The amplified DNA was analyzed by gel electrophoresis on 1% (w/v) agarose gels stained with ethidium bromide.

Figure 5:
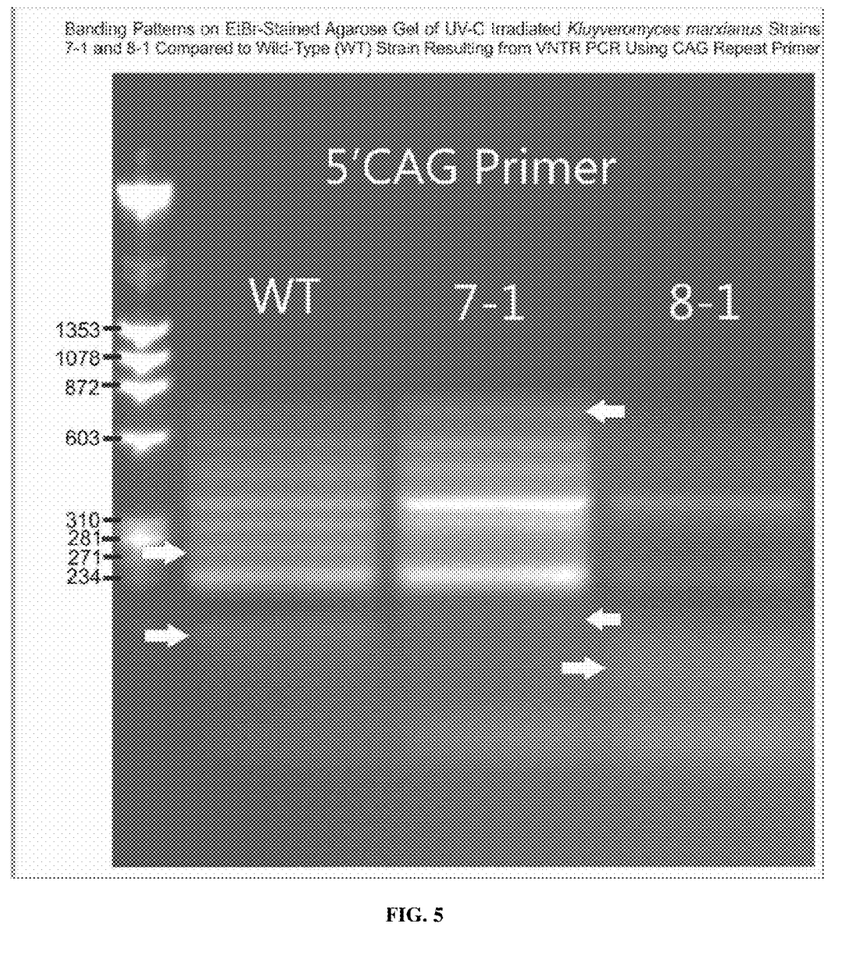
FIG. 5 depicts VNTR fingerprints of genomic DNA of *Kluyveromyces marxianus* mutant strains Y-50798 and Y-50799 compared to *K. marxianus* NRRL Y-1109 wild-type (WT).

The PCR products amplified from the genomic DNA of K. marxianus NRRL Y-1109 wild-type strain and mutant strains Y-50798 and Y-50799 using a variable nucleotide tandem repeat (VNTR) primer produced different banding patterns (fingerprints) when analyzed on an agarose gel (FIG. 5). The arrow on the left at approximately 275 bp points out a band that is present in the fingerprint of the wild-type strain but not detectable in the fingerprints of the mutant strains Y-50798 and Y-50799. The arrow on the right at approximately 750 bp points to a band present in mutant strain Y-50798 but not detectable in the wild-type strain or mutant strain Y-50799. The PCR products from the genomes of the mutant strains are different from each other and from the products from the genome of the wild-type strain.

The differences observed in the PCR products amplified from the genomic DNA of K. marxianus NRRL Y-1109 wild-type strain and mutant strains Y-50798 and Y-50799 using the VNTR sequence as PCR primer demonstrate that the mutant strains are different from each other and from the wild-type strain. VNTR analysis of wild-type and mutant strains Y-50798 and Y-50799 indicated mutations had occurred in the wild-type strain to produce strains Y-50798 and Y-50799.

Example 4

Growth of Strain Y-50798 on Various Substrates at 46° C.

Test tubes containing a mini magnetic stirrer were added 1 mL water, 0.005 g peptone, 0.0025 mg yeast extract, and 0.005 g agar. To tubes 1, 2, 3, and 4 were added, respectively, 0.005 g pectin, 0.005 g D-galacturonic acid, 0.005 g di-galacturonic acid, and 0.005 g tri-galacturonic acid (Sigma Aldrich, St. Louis, Mo., USA). The mixtures were stirred until the solids were dissolved and the solutions were autoclaved for 10 minutes. Tubes were slanted while cooling. A sample comprised of 9 loops of a culture of K. marxianus mutant strain Y-50798 was added to 4 mL of sterile-filtered water, and mixed. After mixing, 0.5 mL of the solution was added to each of the four slant media tubes and the tubes were placed inside an Innova 4230 Incubator Shaker (New Brunswick Scientific, Enfield, Conn., USA) at 47° C. (highest temperature at which this strain still grew well) for 15 days at 100 rpm. Images of the samples were captured using the AlphaImager 3400 system and analyzed using AlphaEase FC software (Alpha Innotech Corporation, San Diego, Calif., USA).

TABLE 1

Growth of mutant strain Y-50798 in a slant-tube assay using pectin as substrate compared to mono-, di-, and tri-D-galacturonic acids as substrates at 47° C. for 15 days at 100 rpm.

| Sample | Integrated density value (IDV)* | % Density of pectin standard (based on IDV) | % Adjusted color density (relative to 20 g/mL pectin standard) |
|---|---|---|---|
| Blank (no strain added) | 11424 | 0.3 | — |
| Pectin | 1109448 | 100.0 | 29.2 |
| Mono-galacturonic acid | 853944 | 76.9 | 22.4 |
| Di-galacturonic acid | 940680 | 84.7 | 24.7 |
| Tri-galacturonic acid | 846940 | 76.3 | 22.2 |

*Images were captured using the AlphaImager 3400 system and analyzed using AlphaEase FC software.

Comparison of Growth of K. marxianus NRRL Y-1109 Wild-Type Strain and Mutant Strains Y-50798 and Y-50799 at 30° C. and 47° C.

Figure 2:
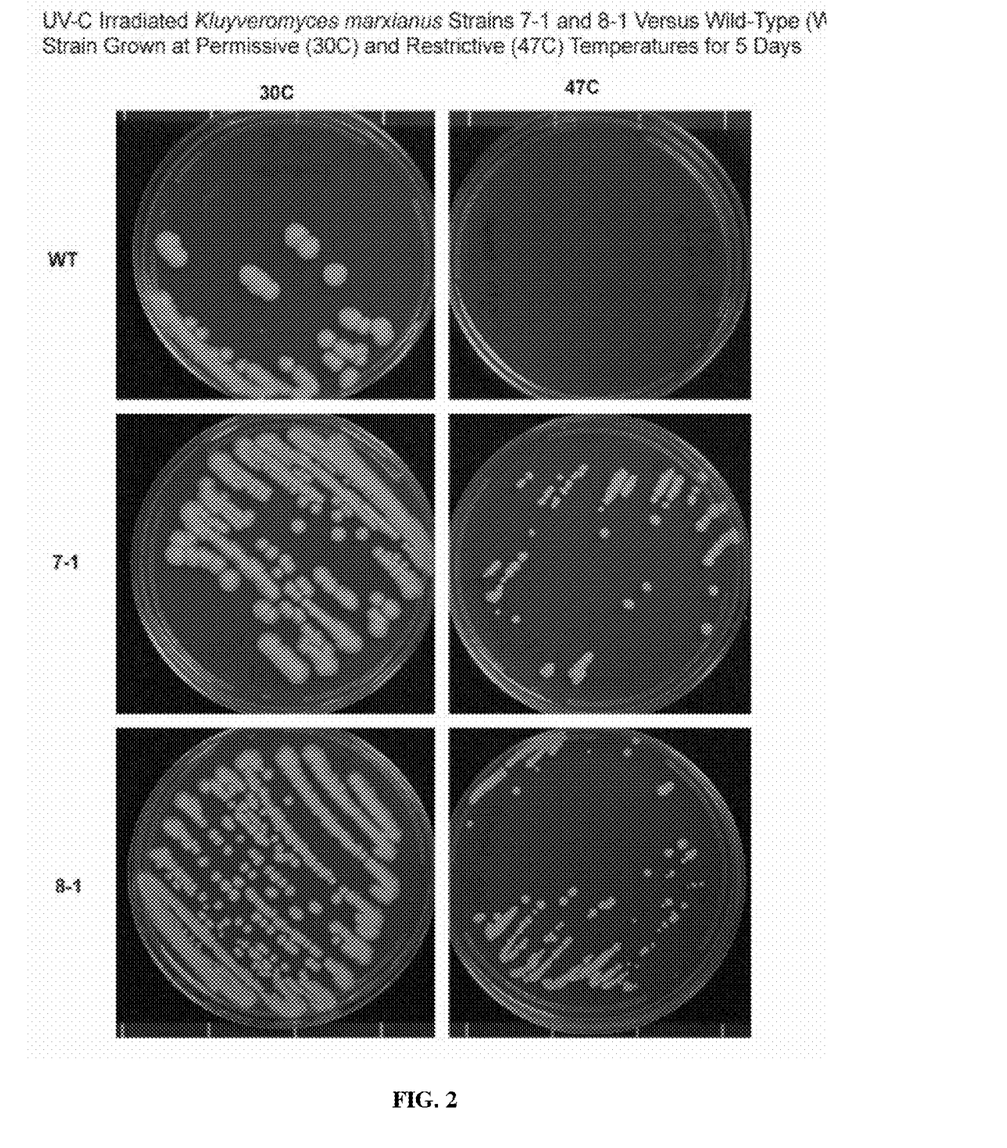
FIG. 2 is a depiction of *Kluyveromyces marxianus* mutant strains NRRL Y-50798 and Y-50799 grown on glucose medium at 30° C. and 47° C. for 5 days under aerobic conditions compared to *K. marxianus* NRRL Y-1109 wild-type (WT).

Growth levels of K. marxianus NRRL Y-1109 wild-type strain and mutant strains Y-50798 and Y-50799 were compared at 30° C. and 47° C. to examine thermotolerance of these strains. The results after the strains were spread on YPD plates and incubated for 5 days at 30° C. and 47° C. are shown in FIG. 2. All strains grew well at 30° C., but only the mutant strains Y-50798 and Y-50799 grew at 47° C. Irradiation of the wild-type strain and selection at elevated temperature produced mutant K. marxianus strains with increased thermotolerance.

Anaerobic and Aerobic Growth on Various Substrates at 46° C. of Mutant Strains Y-50798 and Y-50799 Compared to Wild-Type K. marxianus NRRL Y-1109 and S. cerevisiae NRRL Y-2043

Figure 6:
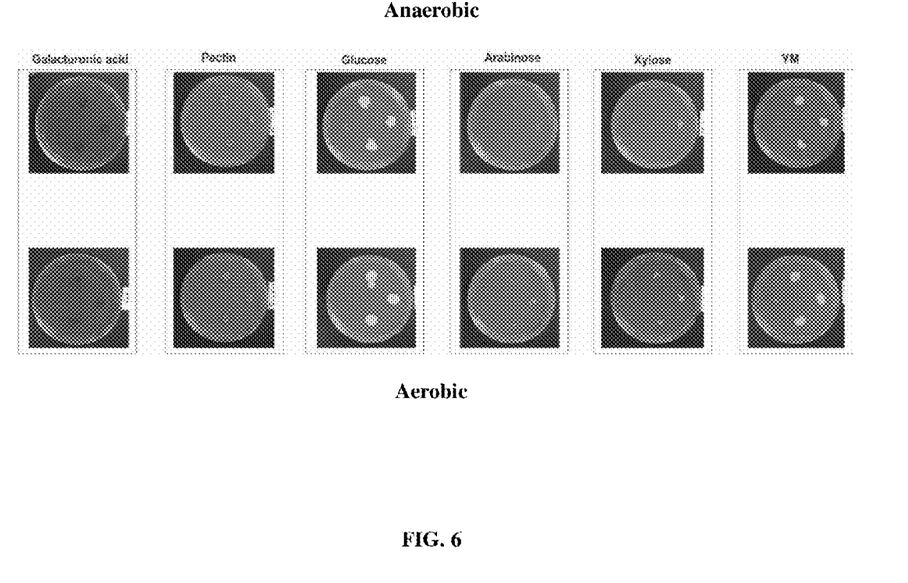
FIG. 6 is a depiction of anaerobic and aerobic growth on selected substrates at 46° C. for 7 days of mutant strains Y-50799 (top position on plate) and Y-50798 (right) compared to wild-type *Kluyveromyces marxianus* NRRL Y-1109 (bottom) and *Saccharomyces cerevisiae* NRRL Y-2043 (left).
Figure 7:
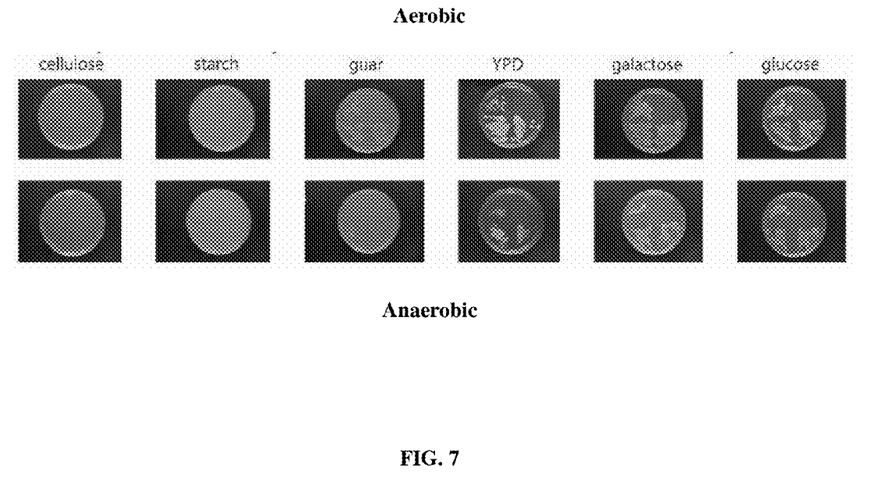
FIG. 7 is a depiction of anaerobic and aerobic growth on additional substrates at 46° C. for 7 days of *Saccharomyces cerevisiae* NRRL Y-2043 (top right position on plate), wild-type *Kluyveromyces marxianus* NRRL Y-1109 (bottom right), and mutant strains Y-50798 (bottom left) and Y-50799 (top left).

The aerobic and anaerobic growth of mutant strains Y-50798 and Y-50799 compared to wild-type K. marxianus NRRL Y-1109 and S. cerevisiae NRRL Y-2043 was examined on various substrates of industrial interest, including galacturonic acid, pectin, glucose, arabinose, xylose (FIG. 6), cellulose, starch, guar, and galactose, (FIG. 7). S. cerevisiae NRRL Y-2043 did not grow at 46° C. on any of these substrates. None of the strains tested grew on untreated cellulose or starch. Wild-type K. marxianus NRRL Y-1109 and mutant strain Y-50799 grew on all other substrates tested except essentially no growth was detected anaerobically on arabinose, xylose, or guar. Mutant strain Y-50798 showed essentially the same results except that it also grew to a detectable extent anaerobically on xylose and guar. Growth on hexose substrates was better than on pentose substrates. The results of the tube assay (Table 1) demonstrate that mutant strain Y-50798 has the ability to grow on pectin and to utilize the resulting mono-, di-, and tri-galacturonic acids to the same extent as the individual acids tested separately.

Example 5

Fermentation of Strains Y-50798, Y-50799 in Braun Reactor

Fermentations with wild-type *K. marxianus* NRRL Y-1109 and mutant strains Y-50798 and Y-50799 were performed in a B. Braun—Sartorius Biostat B reactor (B. Braun Biotech International GmbH (now Sartorius BBI Systems GmbH), Melsungen, Germany). Liquid precultures in YPD medium were incubated at 30° C. for 2 days at 100 rpm. The density of the preculture was adjusted to an absorbance equivalent to 1.0 at 660 nm (Beckman DU 800; Beckman, Indianapolis, Ind., USA), and 20 mL were added to 1 liter of medium in a 1.5-L culture vessel.

In the first stage of the fermentation, ethanol production was measured from YPD medium. The reactor was maintained at 46° C. with stirring (100 rpm) for 3 days with 1 mL/min sparge of filtered nitrogen (dissolved oxygen reading was 0) at a constant pH of 5.5. Samples were collected for ethanol, glucose, melanin, and 2,3-butanediol analysis and the cells were allowed to settle. Spent YPD medium was removed and YPGA medium was added. In the second stage of the fermentation, ethanol production was measured from YPGA medium. The reactor was maintained at 46° C. with stirring (100 rpm) for 7 days with 1 mL/min sparge of filtered nitrogen (dissolved oxygen reading was 0) at a constant pH of 5.5. After the second stage, samples were collected for ethanol, galacturonic acid, melanin, and 2,3-butanediol analysis.

The results presented in Table 2 show that with glucose as the carbon source, the ethanol yield after 3 days at 46° C. was 19% higher for mutant strain Y-50799 than for wild-type *K. marxianus* NRRL Y-1109 (0.51 and 0.43 g ethanol/g glucose, respectively). Cell growth of mutant strain Y-50799 on glucose as measured by OD660 was 2.7 times greater than that of wild-type strain. The cell growth and ethanol yield on glucose were the same for mutant strain Y-50798 and wild type. With galacturonic acid as the carbon source, the ethanol yield after 7 days at 46° C. was 41% higher for mutant strain Y-50798 than for wild-type *K. marxianus* NRRL Y-1109 (0.48 and 0.34 g ethanol/g galacturonic acid, respectively). Cell growth of mutant strain Y-50798 on galacturonic acid as measured by OD660 was 1.3 times greater than that of wild-type strain. The cell growth and ethanol yield on galacturonic acid were the similar for mutant strain Y-50799 and wild type. Both Y-50798 and Y-50799 produced almost a 3-fold increase in melanin production on galacturonic acid over wild type (Y-1109). However, Y-50798 appeared to redirect carbon from 2,3-butanediol production to increase melanin and increase ethanol production unlike Y-50799.

TABLE 2

Cell growth, substrate consumption, and production of ethanol, 2,3-butanediol, and melanin using mutant strains Y-50798 and Y-50799 compared to wild-type *Kluyveromyces marxianus* NRRL Y-1109 (WT) in a Braun-Sartorius Biostat B fermentor at 46° C. under microaerophilic conditions.

| Sample | OD600 | Sugar remaining (g/L) n = 3 | Sugar consumed* (g/L) | Ethanol produced (g/L) n = 3 | Yield (g ethanol/ g sugar) | 2,3-Butanediol (g/L) n = 3 | Melanin (µg/L) n = 2 |
|---|---|---|---|---|---|---|---|
| Glu control | 0.029 | 44.0 ± 0.1 | 0.0 | 0.0 ± 0.0 | | 0.00 ± 0.00 | 0.54 ± 0.04 |
| Glu WT | 0.069 | 3.4 ± 0.1 | 40.6 | 17.5 ± 1.5$^a$ | 0.43 | 1.93 ± 0.02 | 0.67 ± 0.14 |
| Glu 7-1 | 0.067 | 0.0 ± 0.0 | 44.0 | 20.0 ± 7.7 | 0.45 | 1.25 ± 0.04 | 1.04 ± 0.48 |
| Glu 8-1 | 0.190 | 0.0 ± 0.0 | 44.0 | 22.5 ± 1.3$^a$ | 0.51 | 1.95 ± 0.06 | 0.84 ± 0.38 |
| GA control | 0.089 | 42.2 ± 0.02 | 0.0 | 0.0 ± 0.0 | | 0.00 ± 0.00 | 0.54 ± 0.07 |
| GA WT | 0.407 | 1.5 ± 0.01 | 40.7 | 13.9 ± 0.2$^b$ | 0.34 | 1.56 ± 0.03 | 0.64 ± 0.07 |
| GA 7-1 | 0.523 | 0.0 ± 0.0 | 42.2 | 20.5 ± 0.2$^b$ | 0.48 | 1.11 ± 0.06 | 1.67 ± 0.28 |
| GA 8-1 | 0.351 | 0.0 ± 0.0 | 42.2 | 14.8 ± 0.2 | 0.35 | 1.49 ± 0.11 | 1.78 ± 0.67 |

*Fermentation proceeded for 3 days using glucose (Glu) as carbon source. Spent medium was removed, galacturonic acid (GA) medium was added, and fermentation was continued for 7 days using GA as carbon source
$^a$For difference between WT and 8-1, P = 0.014 (calculated using 2-tailed type 2 t-test).
$^b$For difference between WT and 7-1, P < 0.00001 (calculated using 2-tailed type 2 t-test).

To the extent that the term "includes" or "including" is employed in the detailed description or the claims, it is intended to be inclusive in a manner similar to the term "comprising" as that term is interpreted when employed as a transitional word in a claim. Furthermore, to the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

While the invention has been described with reference to details of the illustrated embodiment, these details are not intended to limit the scope of the invention as defined in the appended claims. All cited references and published patent applications cited in this application are incorporated herein by reference. The embodiment of the invention in which exclusive property or privilege is claimed is defined as follows:

The invention claimed is:

1. An isolated *Kluyveromyces marxianus* having been deposited with the United States Department of Agriculture, Agricultural Research Patent Culture Collection as Accession Deposit Number NRRL Y-50798.

2. An isolated *Kluyveromyces marxianus* having been deposited with the United States Department of Agriculture, Agricultural Research Patent Culture Collection as Accession Deposit Number NRRL Y-50799.

3. A method of producing ethanol comprising culturing *Kluyveromyces marxianus* yeast strain NRRL Y-50798 or *Kluyveromyces marxianus* yeast strain NRRL Y-50799 under suitable conditions for a period of time sufficient to allow fermentation of at least a portion of feedstock to produce ethanol.

4. The method of claim 3 in which the conditions include hexose sugars.

5. The method of claim 3 in which the conditions include pentose sugars.

6. The method of claim 3 wherein the yeast strains ferment glucose and xylose at aerobic conditions.

7. The method of claim 3 wherein the feedstock contains galacturonic acid.

8. The method of claim 3 wherein strain grows on a substrate consisting essentially of galacturonic acid, pectin, glucose, arabinose, xylose, and galactose under aerobic conditions.

9. The method of claim 3 wherein strain grows on a substrate comprising of guar.

\* \* \* \* \*